United States Patent [19]
Green et al.

[11] Patent Number: 5,366,134
[45] Date of Patent: * Nov. 22, 1994

[54] SURGICAL FASTENING APPARATUS

[75] Inventors: David T. Green, Westport; Henry Bolanos, East Norwalk; Daniel E. Alesi, Sherman, all of Conn.; Kenneth E. Toso, Port Chester, N.Y.

[73] Assignee: United States Surgical Corporation, Norwalk, Conn.

[*] Notice: The portion of the term of this patent subsequent to Aug. 16, 2011 has been disclaimed.

[21] Appl. No.: 957,246

[22] Filed: Oct. 6, 1992

Related U.S. Application Data

[63] Continuation-in-part of Ser. No. 781,696, Oct. 18, 1991, abandoned, and a continuation-in-part of Ser. No. 778,785, Oct. 18, 1991, abandoned.

[51] Int. Cl.⁵ .......................... A61B 17/068
[52] U.S. Cl. ...................... 227/176; 227/19; 227/182
[58] Field of Search ............. 227/19, 175, 176, 178, 227/180, 181

[56] References Cited

U.S. PATENT DOCUMENTS

| | | |
|---|---|---|
| 2,301,622 | 11/1942 | Hambrecht . |
| 2,853,074 | 9/1958 | Olson . |
| 3,006,344 | 10/1961 | Vogelfanger . |
| 3,082,426 | 3/1963 | Miles . |
| 3,278,107 | 10/1966 | Rygg . |
| 3,604,561 | 9/1971 | Mallina . |
| 4,166,466 | 9/1979 | Jarvik . |
| 4,185,762 | 1/1980 | Froehlich . |
| 4,201,314 | 5/1980 | Samuels et al. . |
| 4,204,623 | 5/1980 | Green . |
| 4,242,902 | 1/1981 | Green . |
| 4,246,903 | 1/1981 | Larkin . |
| 4,296,751 | 10/1981 | Blake, III et al. . |
| 4,325,376 | 4/1982 | Klieman et al. . |
| 4,425,915 | 1/1984 | Ivanov . |
| 4,430,997 | 2/1984 | DiGiovanni et al. . |
| 4,450,839 | 5/1984 | Transue . |
| 4,478,218 | 10/1984 | Mericle . |
| 4,480,640 | 11/1984 | Becht . |
| 4,492,232 | 1/1985 | Green . |
| 4,509,518 | 4/1985 | McGarry et al. . |
| 4,522,207 | 6/1985 | Klieman et al. . |
| 4,557,263 | 12/1985 | Green . |
| 4,562,839 | 1/1986 | Blake, III et al. . |
| 4,565,199 | 1/1986 | Becht . |
| 4,591,086 | 5/1986 | Campbell et al. . |
| 4,944,443 | 7/1090 | Oddsen et al. . |
| 4,967,949 | 11/1990 | Sandhaus . |
| 4,991,763 | 2/1991 | Storace . |
| 5,047,038 | 9/1991 | Peters et al. . |
| 5,049,152 | 9/1991 | Simon et al. . |
| 5,067,958 | 11/1991 | Sanhaus ............... 227/19 X |

FOREIGN PATENT DOCUMENTS

| | | |
|---|---|---|
| 0537757 | 4/1993 | European Pat. Off. . |
| 8302247 | 7/1983 | WIPO ................ 227/19 |

*Primary Examiner*—Rinaldi I. Rada

[57] ABSTRACT

A surgical fastening apparatus comprises first and second handles with an anvil jaw pivotally connected to at least one of the handles for movement from an open to a closed position in response to a first movement of a handle to clamp body tissue. Fastener pushing means are provided for advancing an individual fastener into contact with the anvil jaw in response to a subsequent movement of a handle. An indicator is provided to alert the user to the termination of the first movement; in a preferred embodiment this indicator is a second movement dwell period of the apparatus in which handle movement continues but the anvil jaw remains stationary and the fastener pushing means is not yet actuated. The apparatus further comprises means for preventing incomplete actuation of the fastener pushing means during the subsequent handle movement.

24 Claims, 8 Drawing Sheets

SURGICAL FASTENING APPARATUS

CROSS REFERENCE TO RELATED APPLICATIONS

This application is a continuation-in-part of U.S. Ser. No. 07/781,696 filed Oct. 18, 1991 and U.S. Ser. No. 07/778,785 filed Oct. 18, 1991, both abandoned, which are incorporated by reference herein.

BACKGROUND OF THE INVENTION

1. Field of the Invention

This invention relates to a surgical fastening apparatus, and more particularly to an apparatus for clamping tissue, especially vascular tissue, and subsequently driving an individual fastener through the tissue and into contact with the fastener anvil.

2. Description of the Related Art

Surgical apparatus for applying clips to vascular tissue are well known in the art. In these devices, each leg of the clip, typically U-shaped in configuration, is held in one of the opposing jaws of the instrument and the jaws are placed on sides of the vessel. The jaws are then closed to flatten the clip to squeeze the vessel walls together to effect hemostasis. These prior apparatus suffer from the disadvantage that the clip can only be advanced into the jaws of the instrument when the jaws are open so that vessel clamping and clip closing occur simultaneously. As a result, the surgeon cannot first ensure the vessel is properly clamped before committing to clip closure. Another disadvantage of these clip appliers is they can only be utilized to close a single vessel since they straddle the vessel; they cannot be used to attach approximated vessels or vessel portions.

A known method for repairing vascular tissue is suturing. Although two approximated vessels can be attached by this method, it is not only time consuming, but is difficult to accomplish in certain procedures, especially when the vessel is not in an easily accessible location. Still another disadvantage of suturing is that numerous punctures are made in the vessel walls since a hole is created with each passage of the suture needle.

Instruments for applying single staples one at a time to body tissue are also known. In contrast to clip appliers, these instruments include one jaw which contains a staple and an opposing jaw which has an anvil for deforming the legs of the staple. For example, U.S. Pat. No. 3,278,107 discloses a device where closing of the handles clamps the vessels and forms a single staple. This instrument suffers from the disadvantage associated with the above described clip appliers since clamping of the tissue and application of the staple occur simultaneously. U.S. Pat. No. 3,604,561 also discloses a stapler having a pair of clamping jaws and a mechanism for advancing the staple into an anvil. When sufficient force is applied to the handles, the staple is driven through the tissue and into the anvil. This instrument is deficient in that premature firing could occur if too much force is applied to the handles during the initial clamping action. Additionally, the surgeon cannot readily differentiate when the tissue clamping is completed and the staple firing stroke is initiated within sufficient time to unclamp the tissue. These prior art staplers suffer from the further disadvantage that they permit the handles to be opened and the instrument removed prior to complete staple formation. Thus, a partially formed staple can be left in the patient's body with potential tissue-damaging consequences.

The need therefore exists for an improved surgical fastener which can apply fasteners one at a time to body tissue such as vascular tissue and in which the user can unclamp and/or reposition the tissue in the engaging jaws before firing a fastener. The need also exists for an instrument which can indicate to the user when the tissue clamping action is complete and the fastener firing mechanism is about to be actuated. There is a further need for an instrument which, once fastener firing has begun, can be withdrawn by the user only after fastener formation is completed. Such an instrument could be utilized for closing individual vessels as well as attaching approximated vessels.

SUMMARY OF THE INVENTION

The present invention overcomes the disadvantages and deficiencies of the prior art by providing a surgical fastening apparatus comprising first and second handles and an anvil jaw pivotally connected to one of the handles. The anvil jaw moves between an open position and a closed position to clamp body tissue. Fastener advancing means are provided for advancing an individual fastener into contact with the anvil jaw. Means for closing the anvil and for actuating the fastener advancing means are also provided. In a first movement of the handle the anvil jaw pivots to a closed position. In a subsequent movement of the handle the fastener advancing means is actuated. Between the first and the subsequent movements, an indicator is provided to alert the user that the anvil jaw is closed and the fastener advancing movement is about to begin. Preferably, the indicator comprises a second movement which occurs between the first and subsequent movements. During the second movement the anvil jaw remains stationary and the fastener advancing means is not yet actuated. This second movement constitutes a dwell period of the apparatus.

In a preferred embodiment, camming means is provided for closing the anvil jaw and for actuating the fastener advancing means. A cam plate connects the second handle to the anvil jaw. The cam plate has an angled camming slot cooperating with a pin connected to the second handle. A second camming slot having a driving portion and a guiding portion cooperates with a pin connected to the anvil jaw. As the second handle is approximated, the pin connecting the second handle begins travel along the first camming slot. Simultaneously, the pin connecting the anvil jaw to the cam plate travels in the driving portion to pivot the anvil jaw to a closed position.

A pair of rocker plates connects a fastener pusher to the first handle and to the cam plate. These rocker plates include identical camming slots having guiding and driving portions cooperating with a transverse pin located on the cam plate. During the first and second movements of the apparatus, the pin travels in the respective guiding portions of the camming slots. In the third movement, the pin travels down the respective driving portions of the camming slots, and the fastener pusher advances a fastener into the anvil jaw.

At least a portion of the guiding travel of the pin in the camming slots of the rocker plates coincides with a portion of the guiding travel of the pin in the second camming slot of the cam plate. The length of this coinciding travel path defines an indicator that the first movement has ended; this is referred to as the "dwell period" or the second movement of the apparatus.

To prevent incomplete fastener ejection and deformation, means are provided for preventing de-actuation of the second handle during the third movement of the apparatus. Preferably, this means for preventing comprises a ratchet portion of the second handle adapted to engage a pawl mounted to the first handle. In the beginning of the third movement, the ratchet engages the pawl, preventing deactuation of the second handle. The second handle continues ratcheting upward during the third movement until the fastener is completely formed. At this point, the last ratchet tooth clears the pawl, enabling the handle to move downward to its original position with the anvil jaw open. A coil spring connecting the first handle to the cam plate biases the instrument in the open position.

In another aspect of the present invention, a fastener cartridge is provided comprising a cartridge body adapted to receive a plurality of fasteners in stack form. A spring biased fastener stack pusher contacts the proximal-most fastener. This keeps the fastener stack aligned such that the distal-most fastener in the stack is urged into firing position within the cartridge body. The fastener stack may optionally be aligned at an angle with respect to the longitudinal axis of the instrument. The fastener cartridge may optionally be removably mounted on a handle so that it can be removed and replaced by a loaded cartridge containing the same or different sized fasteners.

BRIEF DESCRIPTION OF THE DRAWINGS:

Preferred embodiments of the invention are described hereinbelow with reference to the drawings wherein.

DETAILED DESCRIPTION OF THE PREFERRED EMBODIMENTS

Figure 1:
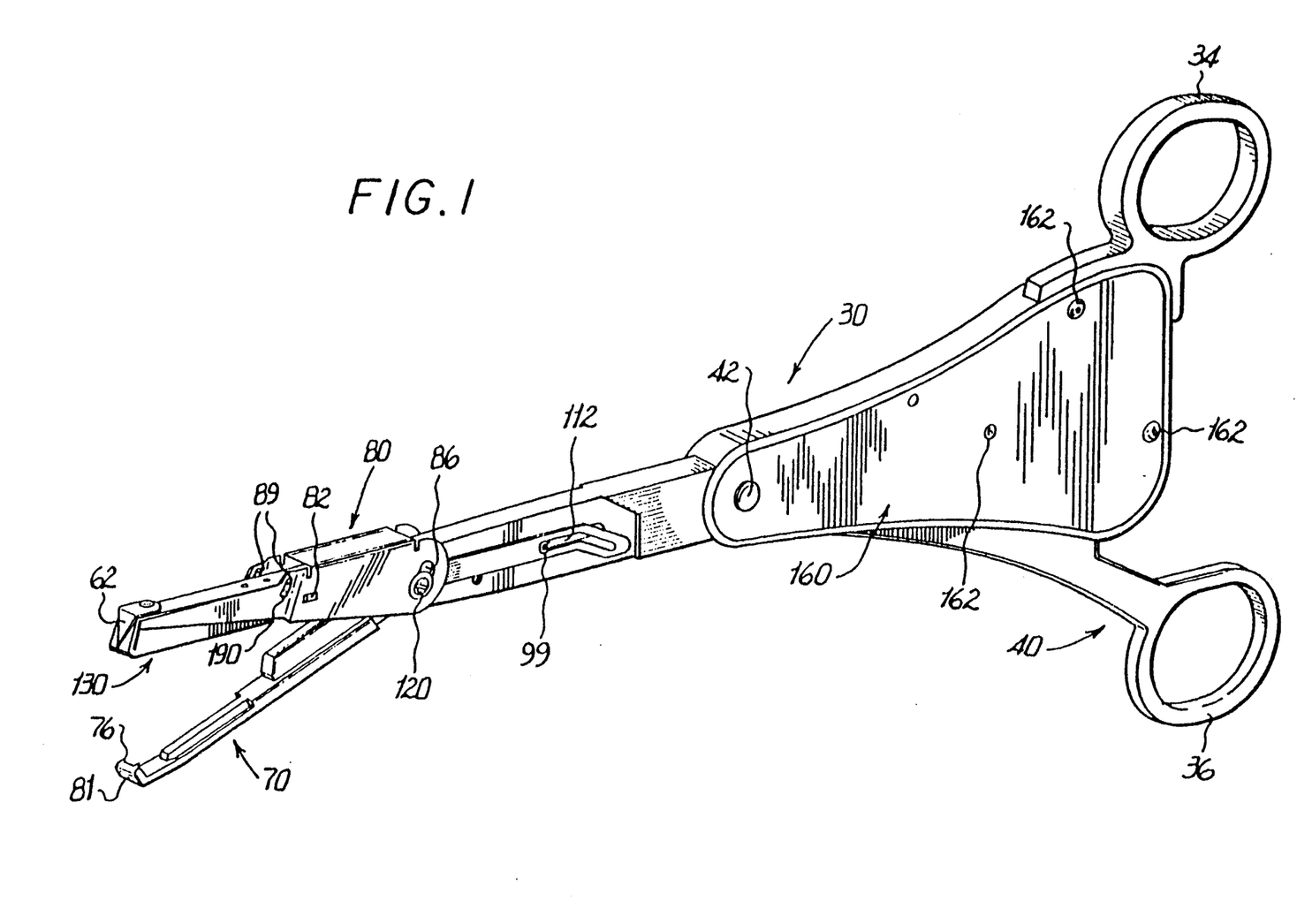
FIG. 1 illustrates a perspective view showing an embodiment of the apparatus of the present invention in the open position.

FIG. 1 illustrates one embodiment of the surgical apparatus of the present invention for driving fasteners one at a time through body tissue and against a fastener anvil. In the drawings, like reference numerals represent identical or similar parts throughout the several views. Briefly, the apparatus comprises a first handle 30 terminating at its distal end in a fastener-carrying jaw 60. A trigger handle 40 is pivotally connected to handle 30 through pivot pin 42. Anvil jaw 70 is positioned opposite fastener-carrying jaw 60 and pivotally connected thereto. Moreover anvil jaw 70 is coupled to trigger handle 40 through a linking member (e.g., cam plate 90 shown in FIG. 2). A fastener pusher 80 is provided for ejecting fasteners one at a time into the body tissue. Pusher 80 is linked to both fastener carrying jaw and cam plate 90 through rocker plates 100 and 110.

Figure 2:
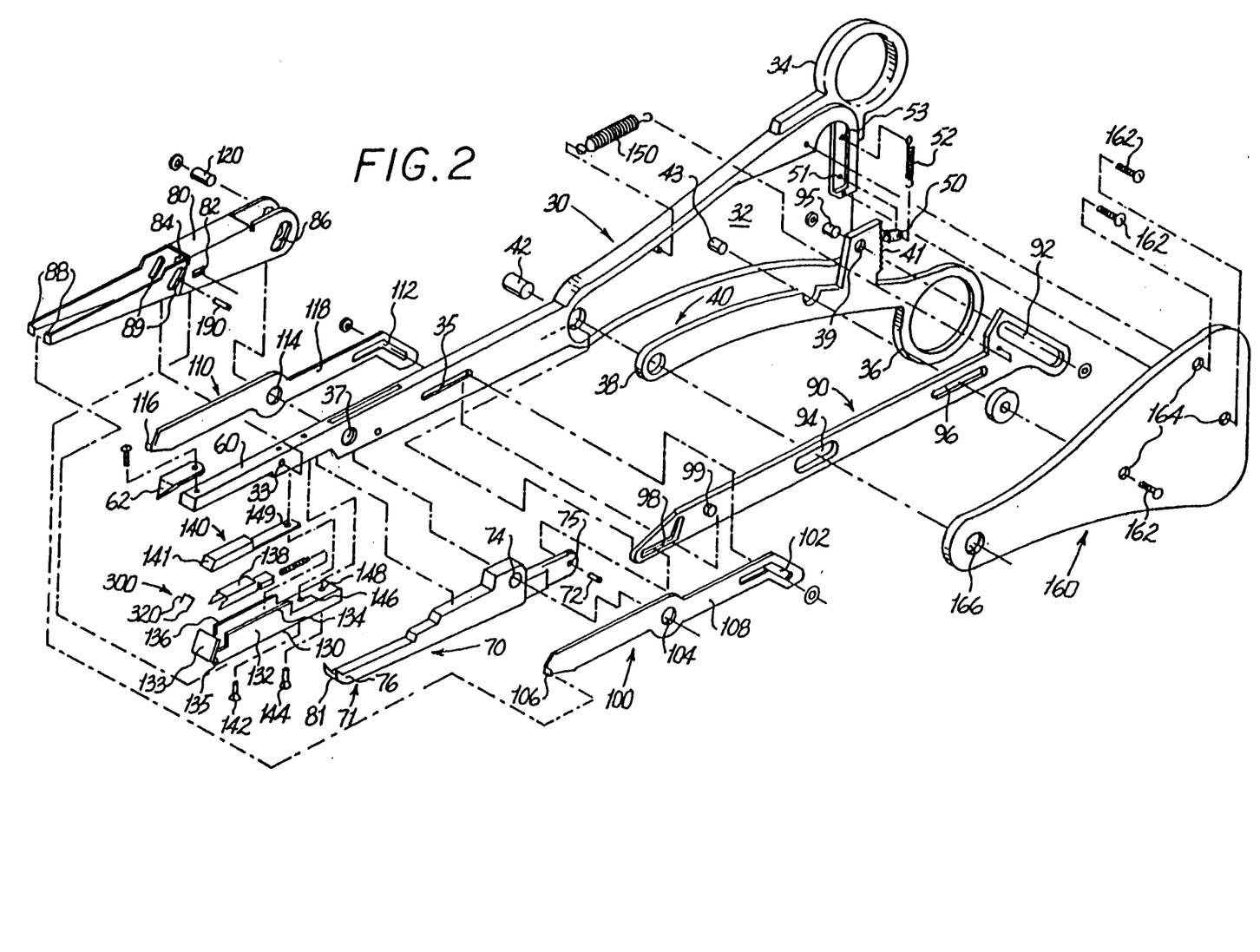
FIG. 2 is an exploded perspective view showing the components of the apparatus of FIG. 1.

FIGS. 2–8 further depict the FIG. 1 embodiment of the surgical apparatus of the present invention adapted for vascular surgery. FIG. 2 illustrates a surgical apparatus having a first handle 30 comprising a main body section 32 terminating at the proximal end in finger loop 34. Finger loop 34 is configured to receive the user's fingers or thumb to facilitate manipulation of the instrument. Handle 30 terminates at its distal end in fastener-carrying jaw 60 configured to receive fastener cartridge 130. Preferably, fastener-carrying jaw 60 further includes a tissue prong 62 for securely gripping body tissue to be fastened. Tissue prong 62 also prevents tissue from entering the instrument during use and interfering with the driving and formation of the fastener.

Fastener carrying-cartridge 130 is mounted on a distal portion of handle 30. Cartridge 130 comprises cartridge body 132 having rails 134, 136 within which are retained a plurality of fasteners 300 in an angled longitudinal stack array. Cartridge body 132 further comprises a front wall 131 angled inwardly to provide a guide path for the fastener pusher 80 as it pushes individual fasteners downwardly through narrow channel 135 (FIG. 5) of the cartridge into body tissue clamped between the jaws. A spring biased stack pusher 138 is positioned in fastener cartridge 130 abutting the proximal-most staple to urge the stack of fasteners distally. Thus the fasteners are fed one at a time into the path of fastener pusher fingers 88 for ejection into body tissue.

A cartridge saddle 140 having an exterior surface 141 is mounted under the fastener stack and fastener pusher 138 within cartridge body 132. The exterior surface 141 of cartridge saddle 140 cooperates with the front wall 133 of cartridge 130 to define channel 135 as the guide path for the fastener.

The cartridge is mounted to distal portion 60 of handle 30 by fasteners 142 and 144 which respectively pass through mounting apertures 146 and 148. Fastener 142 also passes through cartridge saddle mounting aperture 149 to secure the cartridge to the first handle. The fastener cartridge can optionally be removably mounted to the instrument so that it can be removed and replaced by a loaded cartridge containing the same or different sized fasteners.

Figure 3:
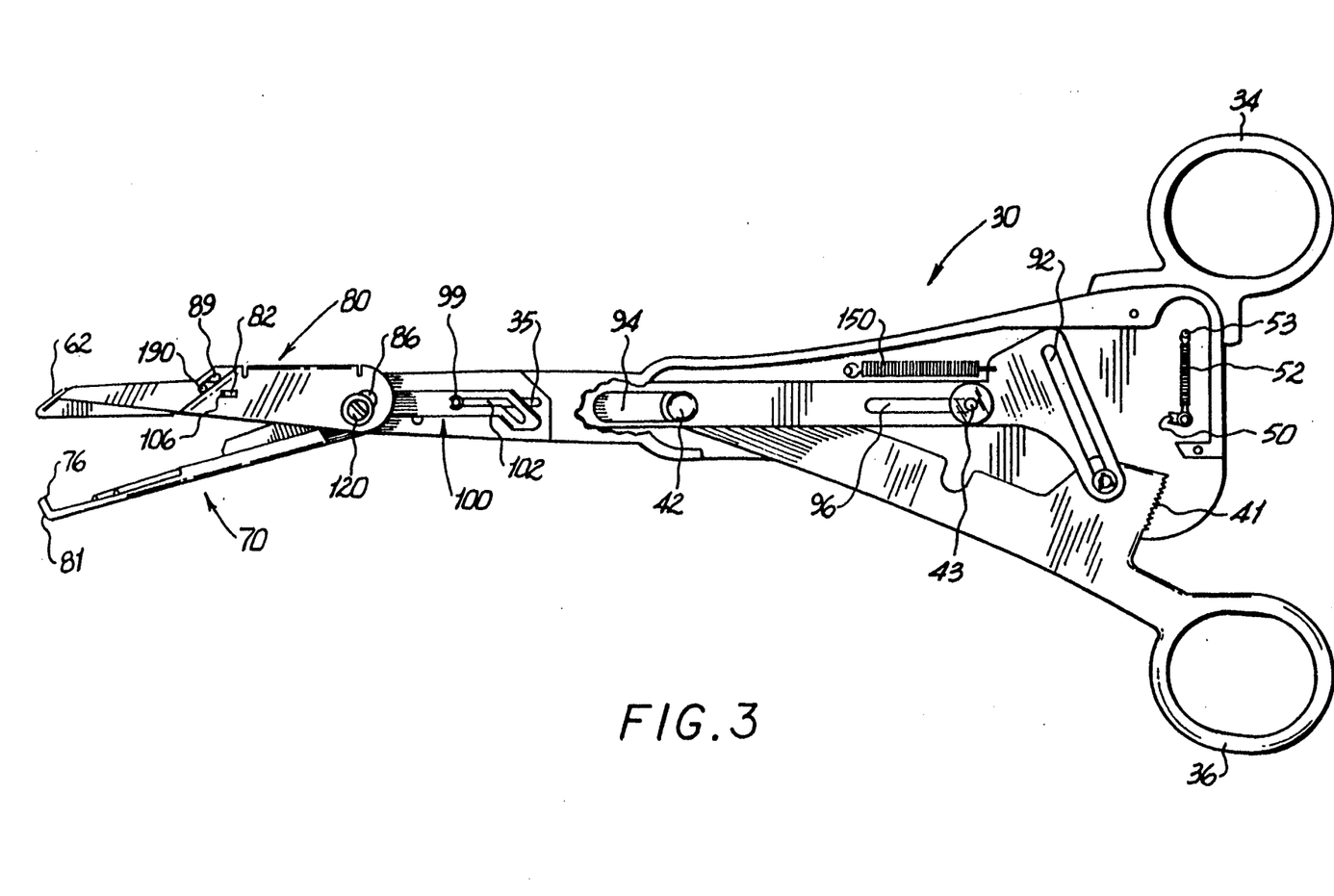
FIG. 3 is a side view in partial cross section of the apparatus in the open position.

As seen in FIGS. 2 and 3, a second handle 40 functions as the trigger handle for actuating the surgical instrument. Trigger handle 40 terminates at its proximal end in finger loop 36 which is in cooperative alignment with finger loop 34. The distal end of trigger handle 40 includes a hole 38 adapted to receive transverse pivot pin 42 for pivotally connecting the handles 30 and 40°

Trigger handle 40 manipulates anvil jaw 70 through the operation of a primary linking member. In this embodiment the linking member is cam plate 90 adapted for longitudinal reciprocal motion within handle 30 in response to relative approximation of finger loops 34 and 36. Cam plate 90 is connected to trigger handle 40 by transverse pin 95 at its proximal end and connected to anvil jaw 70 by transverse pin 72. Cam plate 90 includes a first angled camming slot 92 at its proximal end adapted to engage pin 95 mounted through aperture 39 in trigger handle 40. Operation of pin 95 in camming slot 92 imparts proximal longitudinal motion of cam plate 90 as the trigger handle is actuated.

Cam plate 90 further includes longitudinal guide slots 94 and 96 which respectively cooperate with pivot pin 42 and fixed pin 43 of handle 30 to maintain orientation of the cam plate parallel to the longitudinal axis of the instrument during actuation of the trigger handle 40. The distal end of cam plate 90 includes camming slot 98 having a driving portion and a guiding portion. In this embodiment, the driving portion of camming slot 98 is angled and the guiding portion of camming slot 98 is longitudinal. Pin 72 disposed in aperture 75, connects anvil jaw 70 to camming slot 98 such that when pin 72 travels in the angled portion of the camming slot, the anvil jaw pivots to a closed position.

As depicted in FIG. 2, anvil jaw 70 pivotally connects to fastener-carrying jaw 60 by pin 120, mounted through aperture 74. Anvil jaw 70 includes anvil portion 71 at its distal end. Anvil portion 71 has an inclined wall 81 forming an obtuse angle with the longitudinal axis of anvil jaw 70. The wall 81 may preferably terminate in a pair of tissue prongs 76 to securely grip tissue to be fastened and to prevent this tissue from interfering with fastener formation during firing. A pair of staple forming cups ]70 is formed in inclined wall 81 and is configured to receive staple legs 320 of staple 300 for deforming them around body tissue to assume a B-shaped configuration.

When the surgical fastening apparatus is adapted for use with two-part fasteners such as the two part fasteners disclosed in U.S. Pat. Nos. 4,534,352 and 4,932,960 incorporated herein by reference, anvil jaw 70 can be configured to receive the bottom portion of a two-part fastener for connecting with a fastener top portion ejected by fastener pusher 80. As appreciated by those skilled in the art, when the surgical instrument is adapted for use with two-part fasteners, a portion of anvil jaw 70 is configured to receive connecting base portions of the fasteners for attachment to fastener top portions.

A second linkage mechanism is provided to actuate fastener pusher 80 during the third movement of trigger handle 40. This mechanism comprises a pair of rocker plates 100 and 110 (FIG. 2) which respectively connect cam plate 90 and first handle 30 to the fastener pusher 80. Rocker plates 100 and 110 having arm sections 108 and 118 respectively are provided at their respective proximal ends with identical camming slots 102 and 112 having driving portions and guiding portions. In this embodiment, the driving portions of camming slots 102 and 112 are angled and the guiding portions of camming slots 102 and 112 are longitudinal. The distal ends of rocker plates 100 and 110 terminate in opposed fingers 106 and 116 which engage slots 82 and 84 of fastener pusher 80. Fixed cam pin 99 mounted on cam plate 90 cooperates with camming slots 102 and 112 such that, during the first and second movements of trigger handle 40, pin 99 travels in the longitudinal portions of camming slots 102 and 112.

During the third movement of trigger handle 40, cam pin 99 travels in the angled portion of camming slots 102 and 112. This movement causes rocker plate 100 to rotate downward as finger 106 actuates fastener pusher 80, causing a fastener to be fired. Rocker plates 100 and 110 are pivotally connected by pivot pin 120 to anvil jaw 70, handle 30, and to one another through respective holes 104 and 114 which align with hole 74 in anvil jaw 70 and hole 37 in handle 30.

This embodiment of the present invention provides for fastener, e.g., staple, ejection and formation of a B-shaped staple. A fastener pusher 80 comprises fastener pushing finger 88 at its distal end and a pair of angled camming slots 86 at its proximal end. Camming slots 86 cooperate with pivot pin 120 to attach the fastener pusher to both rocker plates 100 and 110, anvil jaw 70, and fastener-carrying jaw 60. Additional camming slots 89, parallel to camming slots 86, are provided near the center of fastener pusher 80. Camming slots 89 cooperate with pivot pin 190 mounted through aperture 33 of fastener-carrying jaw 60. Fastener pusher 80 further comprises slots 82 and 84 for receiving opposed rocker arm fingers 106 and 116 as previously described.

During the first two movements of trigger handle 40, pin 120 is positioned at the lower distal end of camming slots 86 and pin 190 is positioned at the lower distal end of camming slots 89. During the third movement rocker plate fingers 106 and 116 cause pin 120 to travel to the upper proximal end of camming slots 86 and pin 190 to travel to the upper proximal end of camming slot 89. This forces the fastener pushing finger to contact the distalmost fastener, advance the fastener through tissue, and in the case of a two-part fastener, attach a fastener base to form a completed fastener or, in the case of a staple, deform staple legs against the anvil.

Figure 6:
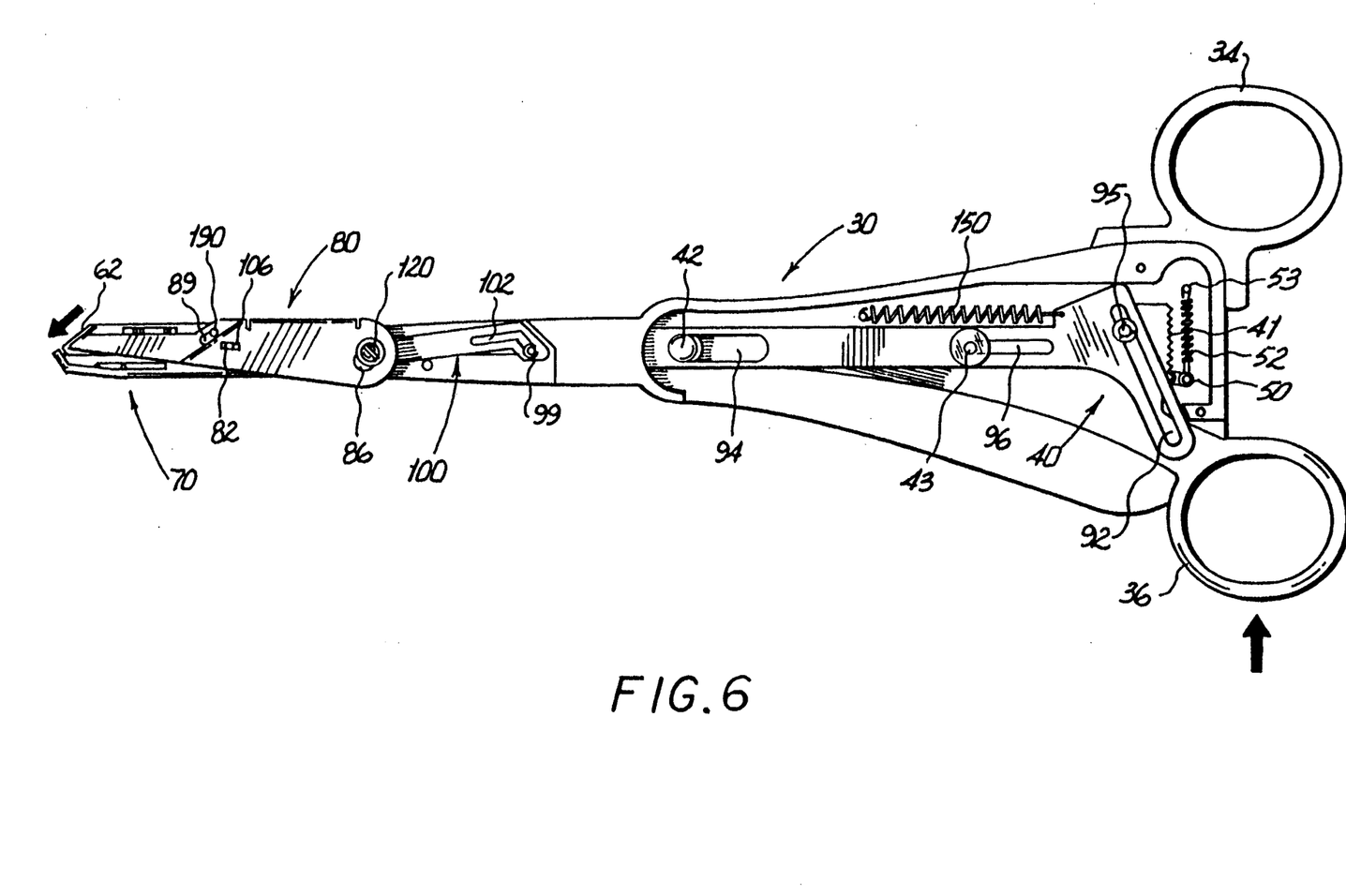
FIG. 6 is a side view in partial cross section of the apparatus showing its internal components with the tissue clamping jaws in the closed position and the fastener pushing means in the last stages of firing a fastener.
Figure 7:
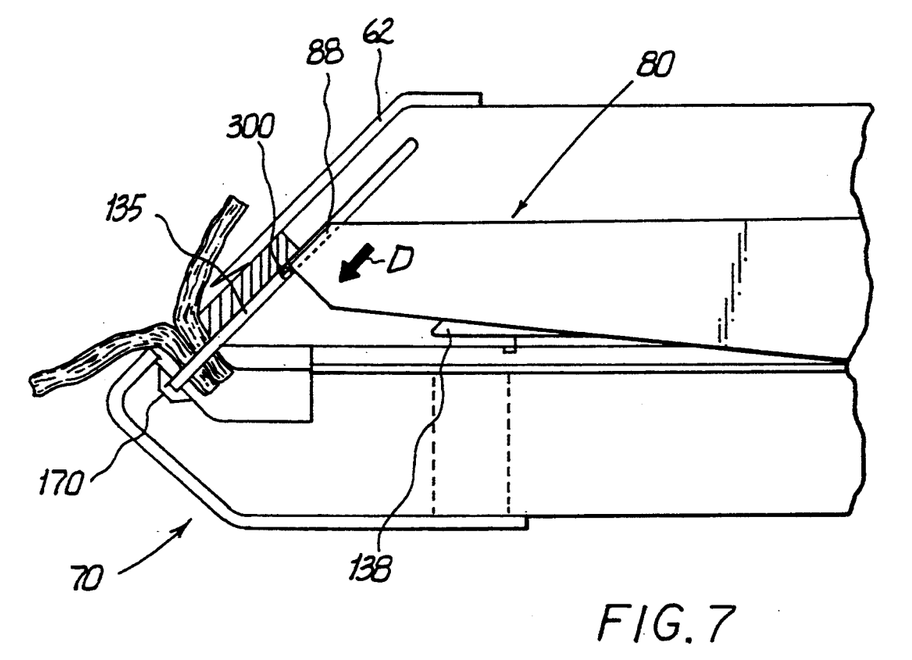
FIG. 7 is an enlarged side view in partial cross section of the distal portion of the apparatus and its internal components showing the fastener pushing means being advanced to fire a fastener.
Figure 8:
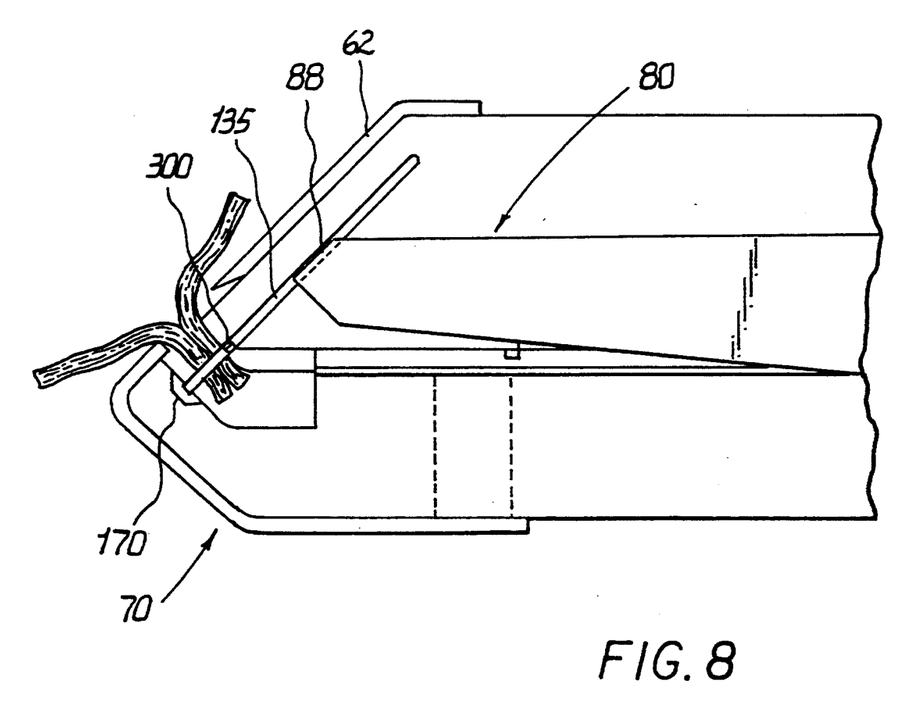
FIG. 8 is an enlarged side view in partial cross section of the distal portion of the apparatus and its internal components showing a staple implanted in the body tissue and the fastener pushing means partially returned to its retracted position.

Referring to FIGS. 2-4 and 6, the surgical apparatus of the present invention also includes a mechanism for preventing incomplete fastener formation during the third movement of trigger handle 40. This mechanism preferably comprises a ratchet and pawl system in which trigger handle 40 includes a ratchet portion 41. A pawl 50 rotates on pin 51 of handle 30 and is connected by coil spring 52 to pin 53 of handle 30. The ratchet portion 41 of trigger handle 40 is configured to engage pawl 50 only during the third movement of the trigger handle, i.e., during fastener firing (FIG. 6).

A handle return mechanism is provided to bias the surgical instrument to its open position (FIG. 3). Coil spring 150 connects handle 30 to cam plate 90. Coil spring 150 biases the cam plate 90 to its distalmost position, forcing trigger handle 40 and anvil jaw 70 to their open positions. As shown in FIGS. 1 and 2, cover 160 mounts to handle 30 through apertures 164 by means of fasteners 162 and by pivot pin 42 mounted through aperture 166.

Figure 9:
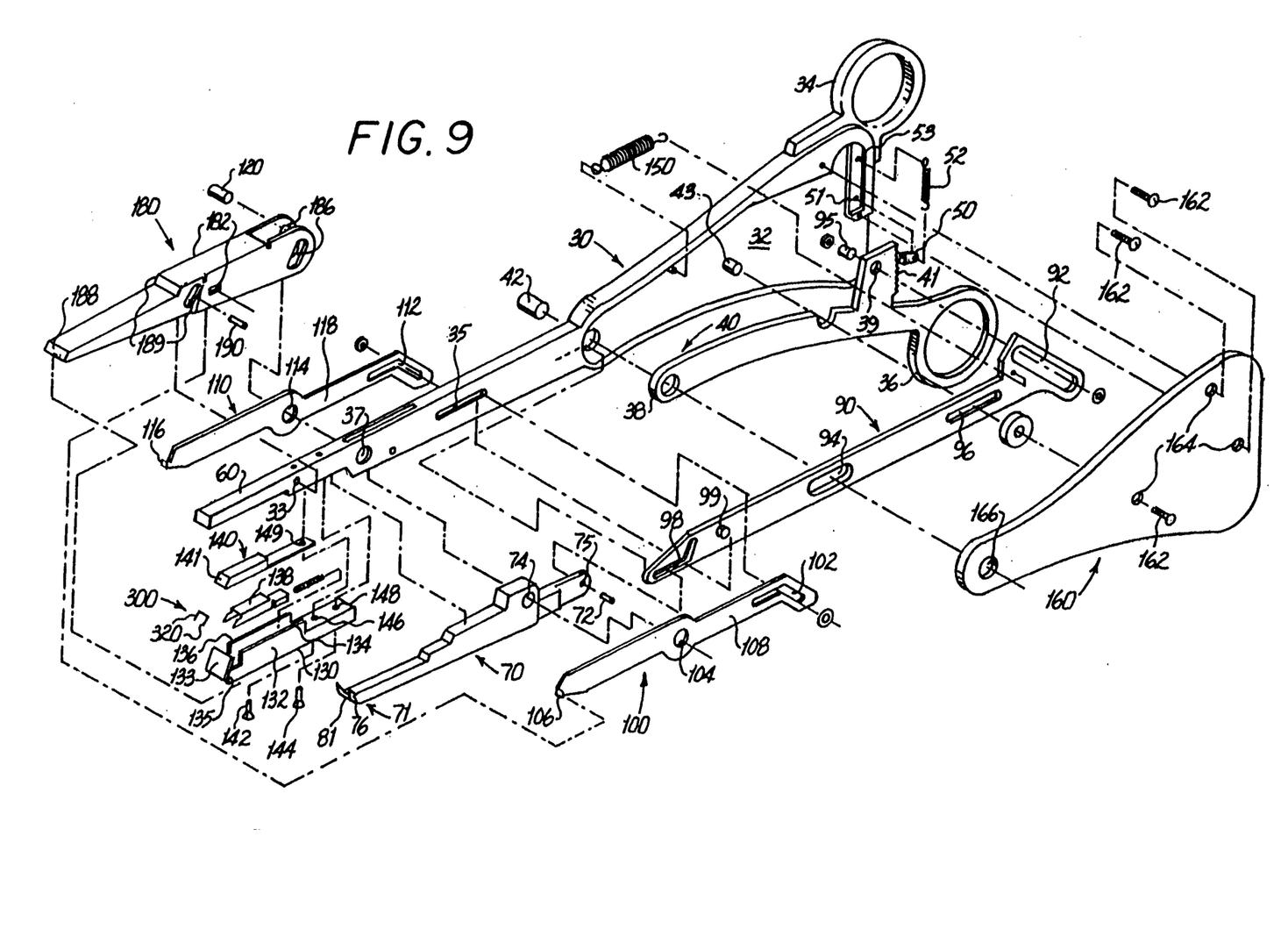
FIG. 9 is an exploded perspective view showing the components of an alternative embodiment of the apparatus of the present invention.

FIG. 9 depicts an alternate embodiment of the surgical fastening apparatus of the present invention. In this embodiment, fastener pusher 180 comprises a fastener pusher finger 188 at its distal end and a pair of angled camming slots 186 at its proximal end. Additional camming slots 189, parallel to camming slots 186, are provided near the center of fastener pusher 180. Fastener pusher 180 further comprises slots 182 for receiving opposed rocker arm fingers 106 and 116 as previously described. The remainder of the elements labelled in FIG. 9 have been described in the discussion of the first embodiment of the present invention.

Turning now to the operation of the instrument of FIG. 1-8, in the open position,. as shown in FIGS. 1 and 3, handles 30 and 40 are spaced apart so that anvil jaw 70 is spaced from fastener carrying =jaw 60. In this position, transverse camming pin 95 is seated in the lowermost, proximal end of angled camming slot 92 of cam plate 90. Also, transverse pivot pin 72 is seated in the uppermost end of the angled portion of camming slot 98 of cam plate 90. Further, pivot pin 42 and fixed pin 43 are seated at the proximal-most ends of respective guide slots 94 and 96 (FIG. 3), thereby positioning cam plate 90 in its initial, distalmost orientation. In this open position, fixed pin 99 of cam plate 90 is situated at the distal-most end of the longitudinal portions of rocker plate camming slots 102 and 112. This configuration maintains fastener pusher 80 in the open, unfired position with pins 120 and 190 seated at the lower distal ends of respective camming slots 86 and 89.

Figure 4:
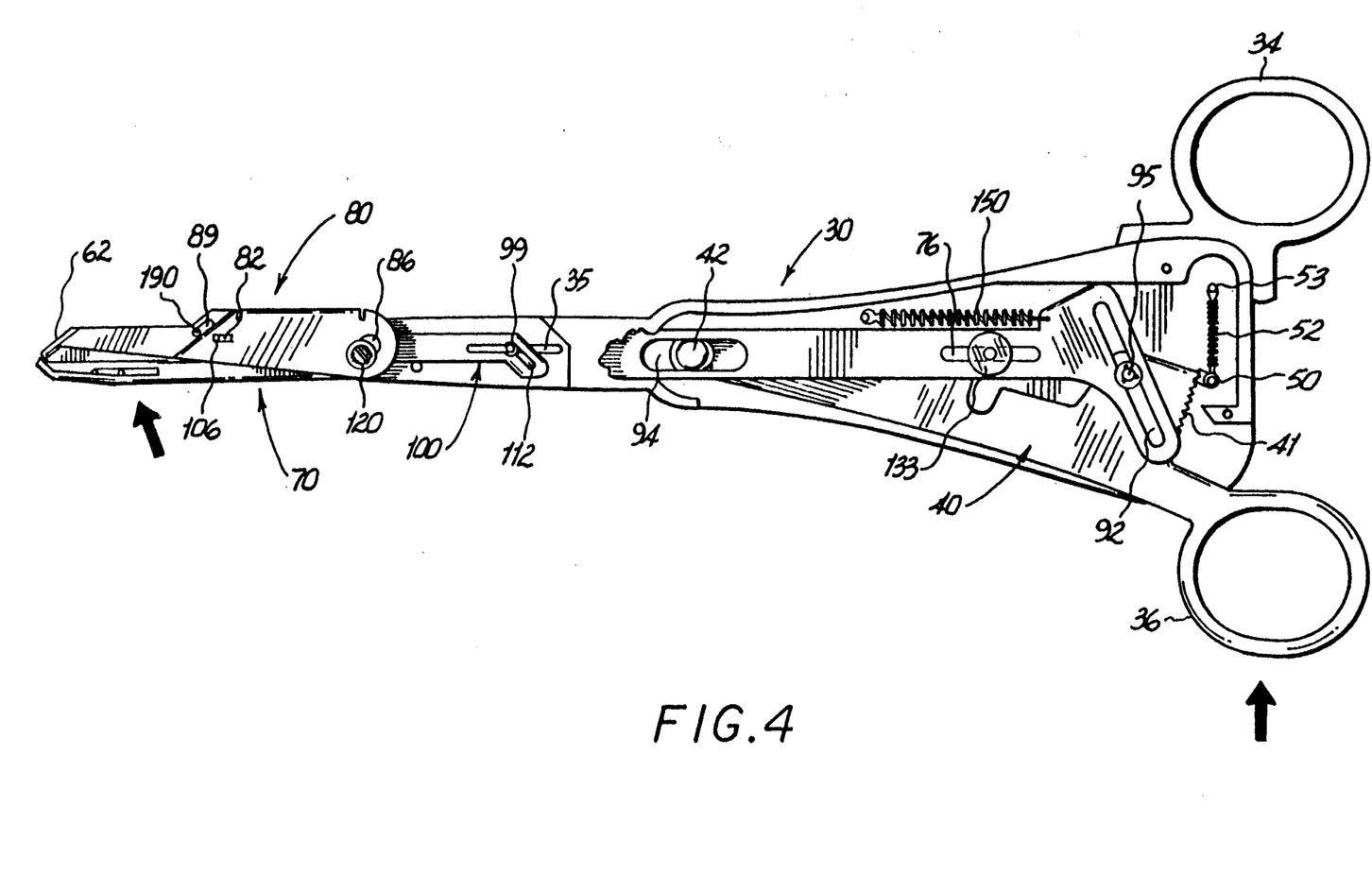
FIG. 4 is a side view in partial cross section of the apparatus showing its internal components with the tissue clamping jaws in the closed position and the fastener pushing means in the unfired position at the beginning of the dwell period.
Figure 5:
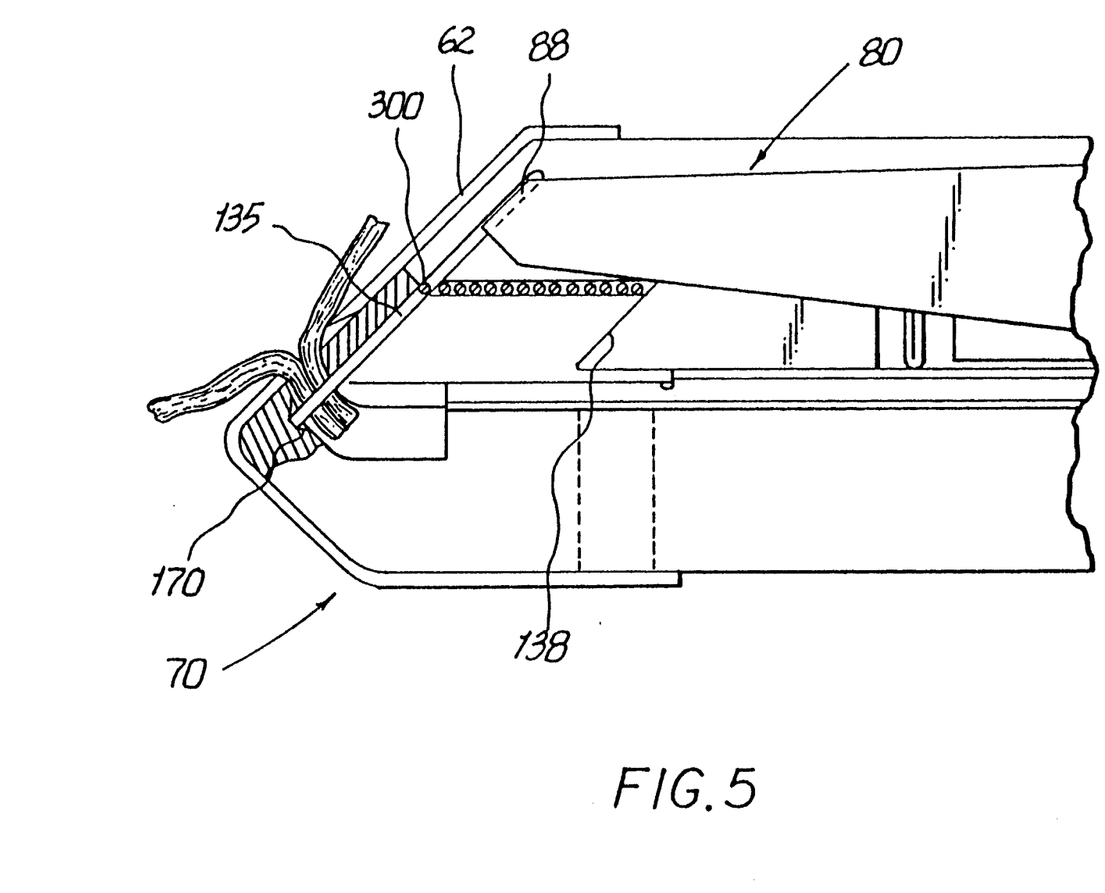
FIG. 5 is an enlarged side view in partial cross section of the distal portion of the apparatus of FIG. 4 showing tissue clamped in the tissue clamping jaws and the fastener pushing means in the unfired position.

Upon initial approximation of trigger handle 40 towards handle 30, transverse pin 95 begins travel diagonally upward in angled camming slot 92. This causes cam plate 90 to move proximally. As a result, pin 72 travels diagonally downward in the angled portion of camming slot 98. This causes anvil jaw 70 to pivot around pivot pin 120 to the closed position (FIG. 4). Thus, tissue is effectively clamped between anvil jaw 70 and fastener carrying jaw 60 (FIG. 5). Note that during this first movement, pin 99 travels along slot 35 while traveling only in the longitudinal portions of respective camming slots 102 and 112. Thus, the fastener firing mechanism has not yet been initiated. This has the advantage that the surgeon can re-open handle 40 to re-clamp the tissue at the same location or at an alternative surgical site.

Once the jaws are in the clamped position and the trigger handle is continuously squeezed, the absence of movement of anvil jaw 70 is felt by the user. This indicates the completion of the clamping cycle and warning that the fastener pushing cycle is about to begin. Thus, in the second movement of handle 40 the jaws remain stationary and the fastener pusher mechanism is not actuated. This dwell period corresponds to the point when camming pin 95 travels along the central portion of camming slot 92 of cam plate 90 while, simultaneously, pin 72 begins travel in the longitudinal portion of camming slot 98 of cam plate 90. Pin 99 continues travel along the longitudinal portions cf camming slots 102 and 112 so that fastener pusher 80 is not actuated by rocker plates 100 and 110. The simultaneous travel of pins 72 and 99 in the longitudinal guiding portions of their respective camming slots corresponds to the dwell period of the apparatus. Note that ratchet portion 41 of trigger handle 40 has not yet engaged pawl 50 leaving the user free to open the trigger handle 40 to unclamp the tissue captured during the first movement of the apparatus. Thus, the dwell period advantageously signals the user that the fastener pushing mechanism will be actuated if the handles continue to be approximated, but provides sufficient time to unclamp the tissue prior to such actuation.

When fastener firing is desired, trigger handle 40 is fully approximated causing pin 95 to travel towards the upper distal-most end of camming slot 92 of cam plate 90. Pin 72 continues to travel along the longitudinal portion of camming slot 98 of cam plate 90 to the distal-most end of the slot (FIG. 6). Simultaneously, pin 99 moves into the angled portions of camming slots 102 and 112. Travel in the angled portions of camming slots 102 and 112 pivots rocker plates 100 and 110. The rocker plates 100 and 110 pivot from an orientation in which arm sections 108 and 118 are parallel to the longitudinal axis of the instrument to an orientation in which arm sections 108 and 118 form an acute angle with the longitudinal axis of the instrument.

The pivotal movement of rocker plates 100 and 110 is translated to sliding movement of pusher 80 along pins 190 and 120 due to the engagement of fingers 106 and 116 in slots 82 and 84. As fingers 106 and 116 slide proximally in respective slots 82 and 84, pusher 80 is forced downwardly towards anvil jaw 70. Also, the camming surface of angled camming slots 86 slides along pin 120 and the camming surfaces of slots 89 slides along pin 190 such that pusher fingers 88 move at an acute angle to the longitudinal axis ("D", FIG. 7).

In the embodiment of FIG. 9, the pivotal movement of rocker plates 100 and 110 is translated to sliding movement of pusher 180 along pins 190 and 120 due to the engagement of fingers 106 and 116 in slots 182. As fingers 106 and 116 slide proximally in slots 182, pusher 180 is forced downwardly towards anvil jaw 70. Also, with the camming surface of angled camming slots 186 slides along pin 120 and the camming surfaces of angled camming slots 89 slides along pin 190 such that pusher finger 188 moves at an acute angle to the longitudinal axis.

The balance of the operation of this embodiment is substantially the same as that described above with respect to FIGS. 1-8.

The surgical apparatus as herein described is preferably constructed as a single use instrument. As such, it is contemplated that the apparatus be economically constructed from materials such as LEXAN TM brand polycarbonate material by General Electric Company and stainless steel. Additionally, the fasteners are constructed from a biocompatible material such as titanium or stainless steel.

The instrument of the present invention has particular application to vascular tissue, although it can be used to attach or close openings in other types of body tissue. The clamping and closing of individual vessels to effect hemostasis by the stapling apparatus of the present invention saves the surgeon valuable time. The stapling apparatus of the present invention can also be used to attach approximated vessel or vessel portions by inserting each leg of the staple through one of the approximated vessels or vessel portions. The B-shaped formation of the legs provides advantageous attachment of the approximated vessels.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:
1. A surgical fastening apparatus comprising:
   first and second handles;
   an anvil jaw pivotally connected to at least one of said handles and movable in response to a first movement of at least one of said handles between an open position and a closed position;

fastener pushing means for advancing an individual fastener into contact with said anvil jaw in response to a subsequent movement of at least one of said handles;

means for tactilely indicating to a user the termination of said first movement, said indicating means including means for providing a dwell period comprising a time during which said handles move between a position in which said anvil jaw is in said closed position and a position in which said fastener pusher means is actuated; and means for preventing incomplete actuation of said fastener pushing means during said subsequent movement.

2. An apparatus as recited in claim 1, further comprising cam means for closing said anvil jaw and for actuating said fastener pushing means.

3. An apparatus as recited in claim 2, wherein said cam means comprises a first link member connecting said second handle to said anvil jaw, wherein said first link member includes a first camming slot cooperating with a first pin connected to said second handle and further includes a second camming slot cooperating with a second pin connected to said anvil jaw.

4. An apparatus as recited in claim 3, wherein said second camming slot has a driving portion and a guiding portion, wherein upon partial approximation of said handles said second pin first travels in said driving portion to pivot said anvil jaw to a closed position.

5. An apparatus as recited in claim 4, further comprising a second link member connecting said first link member to said fastener pushing means, said second link member including a camming slot having guiding and driving portions cooperating with a linking pin connected to said first link member wherein when said linking pin first travels in said guiding portion, said fastener pushing means is not actuated and when said linking pin subsequently travels in said driving portion, said second link member actuates said fastener pushing means.

6. An apparatus as recited in claim 5, wherein during a first movement of the apparatus wherein said handles are approximated, the linking pin connecting the first link member to the second link member begins travel in the guiding portion of the camming slot of the second link member as, simultaneously, the second pin connecting the first link member to the anvil jaw travels in the driving portion of the second camming slot of the first link member, whereby the anvil jaw pivots to a closed position.

7. An apparatus as recited in claim 6, wherein the dwell period is defined by the time of said range of movement between closure and actuation and corresponds to the travel of the second pin connecting the anvil jaw to the first link member and the travel of the linking pin connecting the first link member to the second link member in the guiding portions of their respective camming slots.

8. An apparatus as recited in claim 3, further comprising means for biasing said first link member to a distal position wherein the apparatus is biased to an open position.

9. An apparatus as recited in claim 1, wherein the means for preventing incomplete actuation of the fastener pusher means comprises a ratchet portion of the second handle having a plurality of recesses for receiving a pawl mounted on the first handle wherein the ratchet engages the pawl during the subsequent movement of the apparatus.

10. An apparatus as recited in claim 1 wherein said anvil jaw includes a distal end and wherein said first handle includes a distal end, said apparatus further comprising tissue gripping means located on at least one of the distal end of said first handle and the distal end of said anvil jaw.

11. An apparatus as recited in claim 1, additionally comprising fastener cartridge mounted on said first handle for storing a plurality of fasteners.

12. An apparatus as recited in claim 11, wherein said fastener cartridge is removably mounted on the distal end of said first handle.

13. A surgical fastening apparatus as in claim 1 wherein said handles are movable in at least 3 distinct ranges of progressive approximation stages, wherein said anvil jaw is moved to said closed position during said first range of approximation, said dwell period tactilely recognizable by a user being defined by said second range of approximation wherein said handles are movable into approximation while said anvil jaw remains approximated but said fastener pusher means remains unactuated, and a third range wherein said fastener pusher means is actuated to fire said fastener.

14. A surgical fastening apparatus comprising first and second handles;

an anvil jaw pivotally connected to at least one of said handles for movement between an open position and a closed position;

fastener pusher means for advancing an individual fastener into contact with said anvil jaw;

means for closing the anvil jaw and for actuating said fastener pusher means in a three phase movement wherein in a first relative movement of said handles said anvil jaw pivots to a closed position, in a second subsequent movement of said handles said anvil jaw remains stationary and said fastener pusher means is not yet actuated, and in a third movement of said handles said fastener pusher means is actuated; and means operatively associated with said handles for preventing actuation of said fastener pusher means during said third movement of said handles.

15. An apparatus as recited in claim 14, further comprising cam means for closing said anvil jaw and for actuating said fastener pushing means.

16. An apparatus as recited in claim 15, wherein the cam means comprises a first link member connecting said second handle to said anvil jaw, wherein said first link member includes a first camming slot cooperating with a first pin connected to said second handle and further includes a second camming slot cooperating with a second pin connected to said anvil jaw.

17. An apparatus as recited in claim 16, wherein said second camming slot has a driving portion and a guiding portion, wherein said second pin first travels in said driving portion to pivot said anvil jaw to a closed position.

18. An apparatus as recited in claim 17, further comprising a second link member connecting said first link member to said fastener pushing means, said second link member including a camming slot having guiding and driving portions cooperating with a linking pin connected to said first link member wherein when said linking pin first travels in said guiding portion, said fastener pushing means is not actuated and when said linking pin subsequently travels in said driving portion, said second link member actuates said fastener pushing means.

19. An apparatus as recited in claim 18, wherein during the first movement of the apparatus, the linking pin connecting the first link member to the second link member begins travel in the guiding portions of the respective camming slot of the second link member as, simultaneously, the second pin connecting the first link member to the anvil jaw travels in the driving portion of the second camming slot of the first link member, whereby the anvil jaw pivots to a closed position.

20. An apparatus as recited in claim 14 wherein said anvil jaw includes a distal end and wherein said first handle includes a distal end, said apparatus further comprising tissue gripping means located on at least one of the distal end of said first handle and the distal end of said anvil jaw.

21. An apparatus as recited in claim 14, further comprising a fastener cartridge for storing a plurality of fasteners.

22. An apparatus as recited in claim 14 wherein said first handle includes a distal end, and wherein said fastener cartridge is removably mounted on the distal end of said first handle.

23. A surgical fastening apparatus comprising:
   a first handle;
   a second handle pivotally mounted to said first handle;
   an anvil jaw linked to said second handle for moving said anvil jaw in response to a three phase movement of said second handle wherein in a first relative movement of said second handle said anvil jaw pivots to a closed position in which said anvil jaw contacts the distal end of said first handle causing tissue to be gripped therebetween:
   a fastener cartridge communicating with said first handle, said fastener cartridge containing at least one fastener;
   fastener pusher means linked to said first and second handles comprising a fastener pusher wherein in a second relative movement of said second handle said fastener pusher remains stationary and wherein in a third relative movement of said second handle said fastener pusher moves and contacts said fastener to thereby advance said fastener against said anvil jaw;
   camming means operatively associated with said first and second handles and with said fastener pusher means, said camming means comprising a first camming member wherein during said first relative movement of said second handle said camming means contacts said anvil jaw, during said second relative movement of said second handle said camming means does not contact said fastener pusher means, and wherein during said third relative movement of said second handle said camming means contacts said fastener pusher means: and
   means operatively associated with said handles for preventing incomplete actuation of the fastener pusher means during the third relative movement of said second handle.

24. An apparatus as recited in claim 23, in which said fastener is a staple.

* * * * *